(12) United States Patent
Rath et al.

(10) Patent No.: US 10,968,441 B2
(45) Date of Patent: Apr. 6, 2021

(54) METALLOPROTEINASE-9 OLIGOPEPTIDES AND THEIR THERAPEUTIC USE

(71) Applicant: Matthias W. Rath, Aptos, CA (US)

(72) Inventors: Matthias W. Rath, Heerlen (NL); Aleksandra Niedzwiecki, Aptos, CA (US); Waheed M Roomi, Sunnyvale, CA (US)

(73) Assignee: Matthias W. Rath, Aptos, CA (US)

( * ) Notice: Subject to any disclaimer, the term of this patent is extended or adjusted under 35 U.S.C. 154(b) by 0 days.

(21) Appl. No.: 13/859,748

(22) Filed: Apr. 10, 2013

(65) Prior Publication Data
US 2014/0017225 A1    Jan. 16, 2014

Related U.S. Application Data

(62) Division of application No. 13/549,329, filed on Jul. 13, 2012, now abandoned.

(51) Int. Cl.
| | | |
|---|---|---|
| *C12N 9/50* | (2006.01) | |
| *C12N 9/64* | (2006.01) | |
| *A61K 38/48* | (2006.01) | |

(52) U.S. Cl.
CPC ............ *C12N 9/50* (2013.01); *A61K 38/4886* (2013.01); *C12N 9/6491* (2013.01)

(58) Field of Classification Search
None
See application file for complete search history.

(56) References Cited

U.S. PATENT DOCUMENTS

2003/0139345 A1* 7/2003 Netke et al. .................... 514/12

OTHER PUBLICATIONS

Burkhardt AM et al. Translating translational research: mouse models of human disease. 2013. Cellular & Molecular Immunology. 10. 373-374.*
Heppner GH Tumor Heterogeneity. 1984. Cancer Research. 44. 2259-2265.*
Mak Iwy et al. Lost in translation: animal models and clinical trials in cancer treatment. 2014. American Journal of Translational Research. 6(2). 114-118.*

* cited by examiner

*Primary Examiner* — Paul J Holland
(74) *Attorney, Agent, or Firm* — Geeta Kadambi; Riddhi IP LLC

(57) ABSTRACT

The invention discloses identification and therapeutic use of matrix metalloproteinase oligopeptides, SEQ ID NO: wherein the matrix metalloproteinase oligopeptide is at least one of SEQ ID NO: 7, 11, 12, 18 and 19 and combination thereof. These oligopeptides are bound to antibodies to create an immune response in the subject mammal against the matrix metalloproteinases of various diseases. The instance method is a means of therapeutic intervention against the disease spread created by the matrix metalloproteinases. Further use of these oligopeptide-antibody responses can be extended to any and all diseases that use the matrix metalloproteinases to aid in their pathogenicity.

3 Claims, 14 Drawing Sheets

Specification includes a Sequence Listing.

METALLOPROTEINASE-9 OLIGOPEPTIDES AND THEIR THERAPEUTIC USE

CROSS REFERENCE TO RELATED APPLICATION

The instant application is a divisional application and continuation in part pending U.S. application Ser. No. 13/549,329 filed on Jul. 13, 2012 and claims priority of the same. The disclosure is hereby incorporated by this reference in its entirety for all of their teachings. This application contains sequence listing that has been submitted as an ASCII file named RIPLLC018003CIP2_ST25, the date of creation Jan. 26, 2021, and the size of the ASCII text file in bytes is 5 kb.

FIELD OF TECHNOLOGY

This disclosure relates generally to designing and synthesizing novel matrix metalloproteinase-9 (MMP-9) oligopeptide sequences to be used as therapeutic agents for treating extracellular matrix related diseases. More specifically, this disclosure relates to using the metalloproteinase oligopeptide from various species as a vaccine, a pharmaceutical composition, a therapeutic dose to treat extracellular matrix related diseases that use MMP's.

BACKGROUND

Matrix Metalloproteinases are a family of zinc dependent neutral endopeptidases that play an important role in tumor angiogenesis, tissue remodeling, and cell migration. In cancer, levels of some MMP's are abnormally elevated, enabling cancer cells to degrade the extracellular matrix (ECM), invade the vascular basement membrane, and metastasize to distant sites. A variety of pathological conditions are associated with an increased activity of metalloproteinases (MMP's), in particular MMP-9. These proteases are able to digest collagen and other extracellular matrix (ECM) proteins as a precondition for the spreading of the disease. Thus, there is a need for a therapeutic agent to effectively block these MMP's from digesting the ECM, thereby blocking the spread of cancer and other diseases.

Prevention and treatment of metastasis represents the major challenge in cancer therapy today. The current available treatments are toxic, non-specific and unpredictable for ECM protein affected diseases. There is a need for a therapeutic agent to effectively block the MMP molecules from digesting the ECM, thereby preventing ECM degradation and spreading of diseases.

SUMMARY

The current disclosure discloses a sequence and a composition of MMP-9 oligopeptide and a method of using the MMP-9 oligopeptide as a vaccine, a pharmaceutical composition, a therapeutic dose and as a diagnostic for treating ECM related diseases.

In one embodiment, the oligopeptide analogs for MMP-9 sequences were designed and synthesized. In another embodiment, these oligopeptides were tested for generating immune response in mice using mouse and rat MMP-9 sequences.

In one embodiment, the following oligopeptide sequences were used to produce a vaccine. In another embodiment, a treatment dose may be designed for a person suffering from cancer comprising of SEQ ID NO: 7, 11, 12, 18 and 19 synthetic oligopeptide analogs.

TABLE 1

| | | MMP-9 Synthetic Oligopeptide sequences (Other Species): | | | | | | | | | | | | | | |
|---|---|---|---|---|---|---|---|---|---|---|---|---|---|---|---|---|
| SEQ ID NO:6 | Bovine | MMP-9 A 6 | D | A | D | R | Q | F | G | F | | | | | | |
| SEQ ID NO:7 | Rat | MMP-9 A 7 | D | T | D | R | K | Y | G | F | | | | | | |
| SEQ ID NO:8 | Carp | MMP-9 A 8 | D | K | D | K | I | F | G | F | | | | | | |
| SEQ ID NO:9 | Pufferfish | MMP-9 A 9 | D | K | D | K | K | Y | G | F | | | | | | |
| SEQ ID NO:10 | Rabbit | MMP-9 A 10 | D | T | D | R | R | F | G | F | | | | | | |
| SEQ ID NO:11 | Mouse | MMP-9 A 11 | D | K | D | G | K | F | G | F | | | | | | |
| SEQ ID NO:12 | Rat | MMP-9 A 12 | C | H | F | P | F | T | F | E | G | R | S | Y | L | S | C |
| SEQ ID NO:13 | Chicken | MMP-9 A 13 | C | H | F | P | F | I | F | E | G | R | S | Y | S | R | C |
| SEQ ID NO:14 | European Carp | MMP-9 A 14 | C | H | F | P | F | L | F | E | G | T | S | Y | S | S | C |
| SEQ ID NO:15 | Pufferfish | MMP-9 A 15 | C | H | F | P | F | R | F | Q | N | K | P | Y | K | H | C |
| SEQ ID NO:16 | Flounder | MMP-9 A 16 | C | H | F | P | F | T | F | E | G | K | S | Y | T | S | C |
| SEQ ID NO:17 | Bovine | MMP-9 A 17 | D | Q | D | K | L | Y | G | F | C | P | T | R | V | D | A |
| SEQ ID NO:18 | Rat | MMP-9 A 18 | D | K | A | D | G | F | C | P | T | R | A | D | V | T | V |

TABLE 1-continued

MMP-9 Synthetic Oligopeptide sequences (Other Species):

| | | | | | | | | | | | | | | | | | |
|---|---|---|---|---|---|---|---|---|---|---|---|---|---|---|---|---|---|
| SEQ ID NO:19 | Mouse | MMP-9 A 19 | D | Q | D | K | L | Y | G | F | C | P | T | R | V | D | A |
| SEQ ID NO:20 | Carp | MMP-9 A 20 | D | K | K | Y | G | F | C | P | N | R | D | T | A | V | I |
| SEQ ID NO:21 | Rabbit | MMP-9 A 21 | D | K | D | K | L | Y | G | F | C | P | T | R | A | D | S |

In one embodiment, the sequence of oligopeptide may, but is not limited to, have mutations, deletions and substitutions. The sequences in the submitted sequence list correspond from SEQ ID NO: 2 to 17 of the list. SEQ ID NO: 1 from the text file has been deleted as it was not used in the instant application. Hence SEQ ID NO: 6 corresponds to SEQ 1 of the text file and so on.

In one embodiment, the MMP-9 oligopeptide may be used as a vaccine, a pharmaceutical composition, a therapeutic dose and as a diagnostic tool. In another embodiment, all seventeen oligopeptides may be combined to produce a vaccine.

The oligopeptide sequences, in one embodiment may be either be linear or circular in design. In another embodiment, the oligopeptide may be repeat of sequences.

In another embodiment, the oligopeptide may have either haptens or polyglycans attached to them for efficient delivery.

In another embodiment, a method of immunizing a mammal, such as rat and/or mouse, to raise antibodies for a specific MMP is disclosed. In one embodiment, a selection of an oligopeptide suitable for raising antigenicity is disclosed.

In one embodiment, the immunization of mammals may not be limited to cancer but may include all ECM degradation based disease treatment. In another embodiment, the vaccination may be done once or repeatedly by measuring the antibodies specific to the oligopeptide that was injected. In one embodiment, the specific species may be one of a mammal and/or a non mammal.

In one embodiment, a composition for an oligopeptide as a vaccine and a treatment dose comprising of oligopeptides comprising of SEQ ID NO: 7, 11, 12, 18 and 19 individually or combination thereof.

In one embodiment, the therapeutically effective amount may be rendered, but not limited to, as an injection. Other embodiments may include peroral, subcutaneous, topical, transmucosal, inhalation, subcutaneous, intramuscural, targeted delivery and sustained release formulations. The treatment dose may comprise of therapeutically effective and pharmaceutically acceptable combinations.

The composition, method, and treatment disclosed herein may be implemented in any means for achieving various aspects, and may be executed in a form suitable for the mammal. Other features will be apparent from the accompanying drawings and from the detailed description that follows.

BRIEF DESCRIPTION OF THE DRAWINGS

Example embodiments are illustrated by way of example and not limitation in the figures of the accompanying drawings, in which like references indicate similar elements and in which.

Other features of the present embodiments will be apparent from the accompanying drawings and from the detailed description that follows.

DETAILED DESCRIPTION

Several sequences and methods for immunizing, treating ECM-MMP related pathogenicity and raising an immune response by vaccination are described herein. Although the present embodiments have been described with reference to specific example embodiments, it will be evident that various modifications and changes may be made to these embodiments without departing from the broader spirit and scope of the various embodiments.

Figure 1:
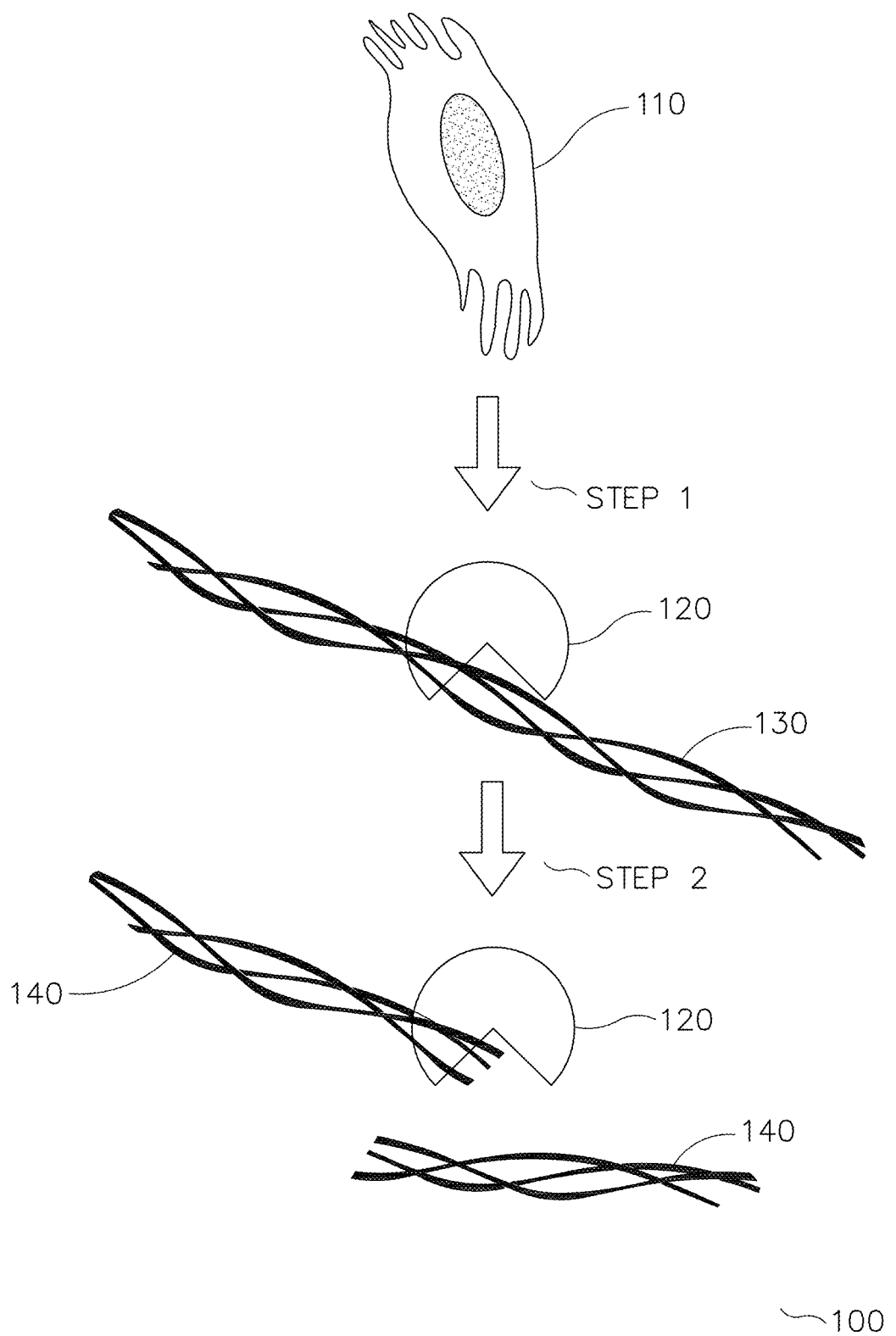
FIG. 1 illustrates the prior art of MMP's digesting the ECM during a disease state.

Cancer cells produce higher levels of matrix metalloproteinases (MMP's), particularly MMP-9. These enzymes are able to digest the extra cellular matrix (ECM) connective tissue surrounding the cancerous cells. MMP's bind to ECM via specific binding sites. Blocking these binding sites in the MMP's prevents the MMP's from binding to ECM. Inhibition of ECM destruction prevents the cancer progression and leads to tumor size reduction. In the current disclosure several potential binding sites were identified within MMP-9. FIG. 1 describes the cancerous cells 110 producing MMP's 120 (step 1). The MMP's 120 bind to the specific binding sites at the ECM 130 (step 2). Step 3 in FIG. 1 shows the MMP's 120 digesting the ECM 140.

Figure 2:
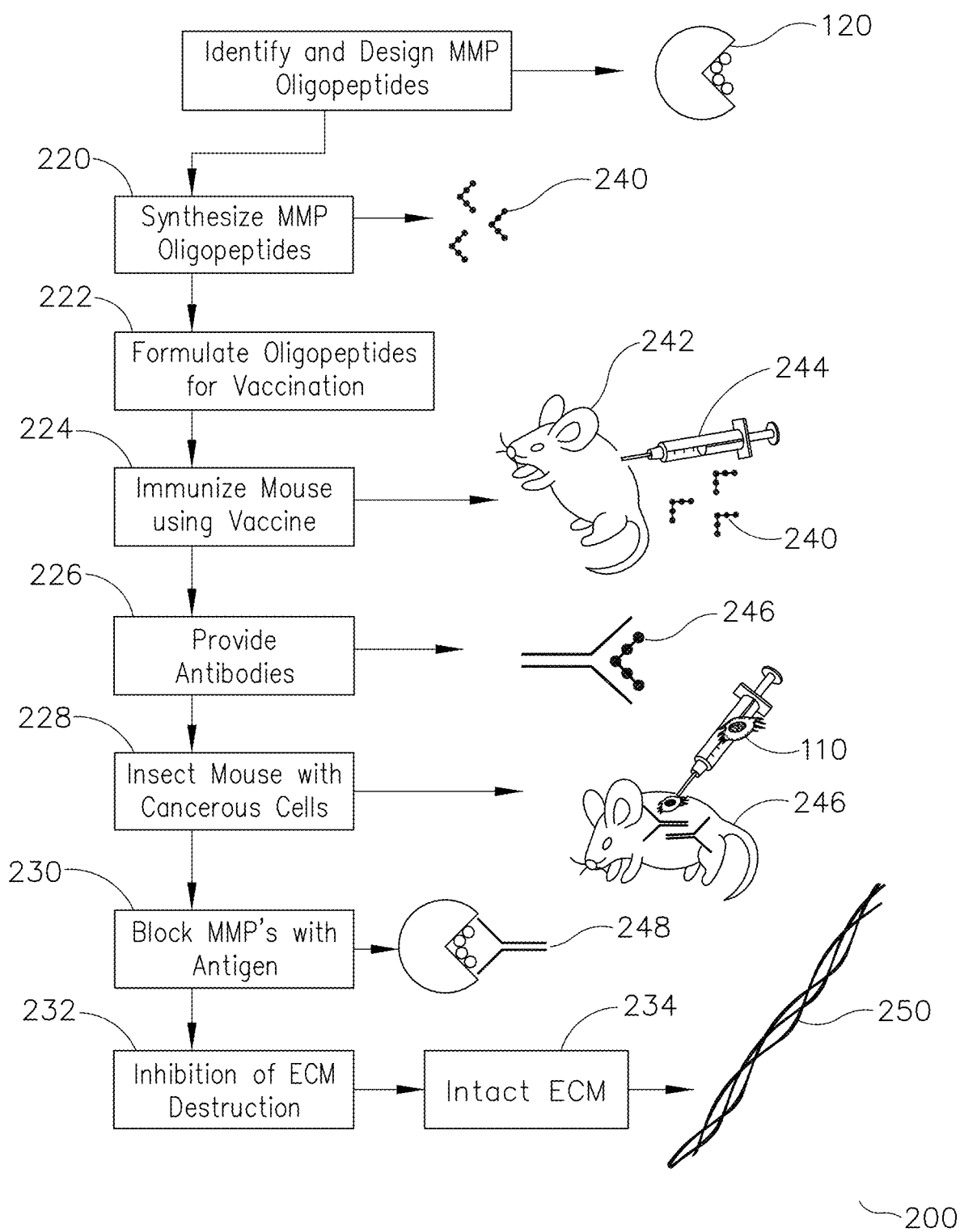
FIG. 2 the method of treating a mammal using the vaccine.

FIG. 2 explains the current disclosure in steps of vaccine production and immunization 200. Identification and design of the MMP's are carried out 210 using the MMP sequences. Oligopeptides are synthesized 220 and represented by synthetic oligopeptides 240. The formulate oligopeptides for vaccination are 222. The antibodies are produced as shown in 226. The mouse 242 is immunized 224 using vaccine with syringe 240. The oligopeptides may be of specific length. Several permutations and combinations of the sequences were tested. The instant disclosure sequences are shown below as MMP-9 SEQ ID NO:6-21. Prior to the selection of these seventeen sequences as potential oligopeptides, several potential binding sites for MMP-9 were identified. Finally a total of seventeen oligopeptides were synthesized and tested on mouse. The MMP-9 SEQ IDNO: 6-21 was synthesized in a linear and circular format. Many modifications for these sequences were also done in one embodiment. The modifications were substituting one or more amino acid residues at N-terminal, C-terminal and both C and N terminals, substitution of amino acid residues based on similar charge and polarity, without consideration of charge and polarity, omitting of amino acids in C and N terminal, omitting only in C-terminal and only in N-terminal.

In another embodiment, substitution and omission may be carried out simultaneously. The oligopeptides may be further modified by repeating the sequences and combining more than one SEQ ID NO: 6-21 for producing and formulating a vaccine. The peptidomimetic to the MMP's may be used to block the binding site of an over expressed MMP in a specific disease.

In one embodiment, the oligopeptide may be used as feedback regulators to specifically prevent or reduce the synthesis rate of MMP-9 productions at the cellular level. In one embodiment process of blocking and inhibition of ECM destruction by antigens produced due to vaccination of mouse and rat.

Preparation of Peptide Solutions for Immunization

The design of the experiment was done such that Peptides are dissolved at concentration 1.1 mg/ml. Conjugate Streptavidin-HRP as a carrier protein was dissolved in PBS at concentration 0.8 mg/ml. Peptide solution was mixed with conjugate Streptavidin-HRP to achieve standard final concentrations for peptides and conjugate.

Conjugate Streptavidin-PolyHRP20 (#SP20C) as a carrier protein was purchased from SDT (Germany), dialysis tubing cellulose membrane D9777-100FT, Sigma (St. Louis, Mo.), glass vials ISO 8362-1 2R-CL-1 (Medical Glass, Bratislava, Slovakia) or PP Costar Microcentrifuge Tube (Cat. #3621, Corning Inc., USA), urea and salts were obtained from Fluka (Schweiz). All the reagents used were of analytical grade. All solutions were prepared using pyrogen free milliQ grade water. "SP-35" from gp41 env HIV-1 was used as a Reference peptide with biotin having the following sequence SEQ ID NO: 22: H-Arg-Ile-Leu-Ala-Val-Glu-Arg-Tyr-Leu-Lys-Asp-Gln-Gln-Leu-Leu-Gly-Ile-Trp-Gly-Cys-Ser-Gly-Lys-Leu-Ile-Cys-Thr-Thr-Ala-Val-Pro-Trp-Asn-Ala-Ser-OH.

Testing of peptide solubility: Data for peptide solubility are represented in Table 2 and 3. Peptides SEQ ID 6-21 was dissolved in 8M Urea to a final concentration of 1.1 mg/ml.

TABLE 2

MMP 9 Peptides from various species: Solubility test

| Peptide | Weight, mg | 8M Urea, ml | Solubility |
|---|---|---|---|
| SEQ ID NO:6 | 0.37 | 0.405 | Soluble |
| SEQ ID NO:7 | 0.69 | 0.76 | Soluble |
| SEQ ID NO:8 | 0.38 | 0.42 | Soluble |
| SEQ ID NO:9 | 0.62 | 0.68 | Soluble |
| SEQ ID NO:10 | 0.56 | 0.515 | Soluble |
| SEQ ID NO:11 | 0.53 | 0.585 | Soluble |
| SEQ ID NO:12 | 0.43 | 0.475 | Insoluble |
| SEQ ID NO:13 | 0.64 | 0.705 | Soluble |
| SEQ ID NO:14 | 0.44 | 0.485 | Soluble |
| SEQ ID NO:15 | 0.51 | 0.56 | Soluble |
| SEQ ID NO:16 | 0.5 | 0.55 | Soluble |
| SEQ ID NO:17 | 0.58 | 0.64 | Soluble |
| SEQ ID NO:18 | 0.57 | 0.625 | Soluble |
| SEQ ID NO:19 | 0.65 | 0.715 | Soluble |
| SEQ ID NO:20 | 0.48 | 0.53 | Soluble |
| SEQ ID NO:21 | 0.63 | 0.695 | Soluble |

TABLE 3

MMP 9 Peptide SEQ ID 12 was insoluble in 8M Urea hence equal volume of 0.1M Na-carbonate buffer, pH 9.5 were added to dissolve it in a solution as shown in Table 2.

| Peptide | Weight, mg | 8M Urea, ml | Additional solution, ml | Solubility |
|---|---|---|---|---|
| SEQ ID NO:#6 | 4.63 | 1.445 | | Soluble |
| SEQ ID NO:#7 | 4.82 | 1.505 | | Soluble |
| SEQ ID NO:#8 | 4.29 | 1.34 | | Soluble |
| SEQ ID NO:#9 | 4.85 | 1.515 | | Soluble |
| SEQ ID NO:#10 | 4.44 | 1.39 | | Soluble |
| SEQ ID NO:#11 | 4.63 | 1.445 | | Soluble |
| SEQ ID NO:#12 | 4.54 | 0.71 | 0.71 ml 0.1M Na-carbonate buffer, pH 9.5 | Soluble |
| SEQ ID NO:#13 | 4.75 | 1.485 | | Soluble |
| SEQ ID NO:#14 | 4.54 | 1.42 | | Soluble |
| SEQ ID NO:#15 | 4.56 | 1.425 | | Soluble |
| SEQ ID NO:#16 | 4.75 | 1.485 | | Soluble |
| SEQ ID NO:#17 | 4.27 | 1.335 | | Soluble |
| SEQ ID NO:#18 | 4.32 | 1.35 | | Soluble |
| SEQ ID NO:#19 | 4.54 | 1.42 | | Soluble |
| SEQ ID NO:#20 | 4.53 | 1.415 | | Soluble |
| SEQ ID NO:#21 | 4.54 | 1.42 | | Soluble |
| SP35 | 4.29 | 1.34 | | Soluble |

Preparation of Conjugate Streptavidin-PolyHRP20 as a carrier protein. Conventionally the conjugate Streptavidin-PolyHRP20 (Str-HRP 1 mg/ml) comes as solution containing 50% (v/v) glycerol. For removing the glycerol, Str-HRP was dialyzed against Phosphate buffer saline (PBS). Volume of conjugate increases after dialysis and it has to be concentrated to a final volume containing 1.25 (0.8 mg/ml) concentration.

Preparation of Conjugate Peptide with Carrier Protein

Peptides were dissolved in appropriate volume 8M Urea and additional solution. Final concentration of peptide-Str-HRP solution was 0.8 mg/ml and 0.6 mg/ml for peptide and Str-HRP, respectively. After dissolving, 4 aliquotes in 0.2 ml portions were taken from each peptide solution, mixed with 0.6 ml Str-HRP and incubated over night at +4° C. Conjugate peptide with carrier protein (Str-HRP) was frozen and stored at −20° C. until further use. Final concentration of urea in peptide-Str-HRP solution was 2M for all peptides.

Immunization

BALB/c female mouse, complete Freund's adjuvant (Calbiochem, USA), incomplete Freund's adjuvant (Calbiochem, USA), 2 ml syringe 22 G×1½" (BKMI, R. Korea), PP Costar Microcentrifuge Tube (Cat. #3621, Corning Inc., USA), Vortex Vibrofix VF1 (IKA-Werk, Germany), GP Centrifuge (Beckman, USA) were used as materials.

The pattern for immunization was as follows:
Day 0: Immunization with complete Freund's adjuvant
Day 7: Booster with incomplete Freund's adjuvant
Day 14: Booster with incomplete Freund's adjuvant
Day 28: Booster with incomplete Freund's adjuvant
Day 38: Terminal bleed Method of Immunization: Frozen 0.8 ml aliquotes of peptide+Str-HRP conjugate were thawed at room temperature (RT) and mixed with 0.8 ml of appropriate adjuvant. Adjuvant was added and mixed by vortexing immediately before injections were given. Immunization was done by using intra peritoneal injections with 100 μg peptide per animal in final volume 250 μl of 1:1 (v:v) peptide+Str-HRP: adjuvant. Six animals were used per peptide.

Preparation of serum: At 38 days, the mouse was bled. Blood was collected in 2-ml microcentrifuge tube and the blood was allowed to clot at room temperature for 1 hour. Centrifugation using the microcentrifuge tube with the clot inside was done for 15 min at 2500 g and serum was collected. Volume for each sample was no less than 400 μl. The serum was stored at −20° C.

Testing immune response to individual peptide: Determination of mouse antibodies to peptide based on indirect solid-phase immunoenzymatic assay with avidin on solid-phase was performed.

Test procedure: Peptides for binding on the avidin-coated plate were taken from test-solution for determining the solubility of peptides (Table 2 and 3) and were dissolved up to 2 mM in sample diluents immediately before the test procedure as shown in Table 4.

TABLE 4

| Peptide | Mol Weight | 2 mM mg/ml | μl peptides solution 1.1 mg/ml on 10 ml sample diluent |
| --- | --- | --- | --- |
| SEQ ID NO:#6 | 1294.44 | 2.589 | 23.5 |
| SEQ ID NO:#7 | 1340.51 | 2.681 | 24.5 |
| SEQ ID NO:#8 | 1308.55 | 2.617 | 24 |
| SEQ ID NO:#9 | 1339.57 | 2.679 | 24.5 |
| SEQ ID NO:#10 | 1352.52 | 2.705 | 24.5 |
| SEQ ID NO:#11 | 1254.44 | 2.509 | 23 |
| SEQ ID NO:#12 | 2133.48 | 4.267 | 39 |
| SEQ ID NO:#13 | 2188.56 | 4.377 | 40 |
| SEQ ID NO:#14 | 2064.37 | 4.129 | 37.5 |
| SEQ ID NO:#15 | 2291.73 | 4.583 | 42 |
| SEQ ID NO:#16 | 2093.41 | 4.187 | 38 |
| SEQ ID NO:#17 | 2067.36 | 4.135 | 37.5 |
| SEQ ID NO:#18 | 1934.21 | 3.868 | 35 |
| SEQ ID NO:#19 | 2067.36 | 4.135 | 37.5 |
| SEQ ID NO:#20 | 2066.41 | 4.133 | 37.5 |
| SEQ ID NO:#21 | 2055.34 | 4.111 | 37.5 |
| SP35 | 3702.6 | 7.405 | 67 |

EIA plates were coated by adding to a well containing 100 μl of avidin dissolved 10 μg/ml in 50 mM carbonate buffer, pH 9.5 and incubated for 20 h at 20° C. The plates were washed 4 times with wash fluid. Peptides 2 mM, 100 ml/well in sample diluent and incubated 60 min at 37° C. Control wells contain avidin. The plates were washed 4 times with wash fluid. Serum from each mouse and negative control were diluted 1:100, 1:1000 and 1:10000 in sample diluents and were added to the wells, coated by the corresponding peptide (100 μl per well) and incubated for 1 h at 37° C. The plates were washed 4 times with wash fluid. Conjugates of rabbit anti-mouse IgG antibody with HRPO (dilution of 1:3000 in conjugate diluent) were added to the wells (100 viper well). The plates were incubated for 0.5 h at 37° C. The plates were washed 4 times with wash fluid. 100 μl of freshly prepared substrate solution (1 v TMB solution+7 v substrate buffer) were added to each well, and the plates were left at room temperature for 15 minutes in a dark place. A blue color should develop in wells containing positive samples. 100 μl stop solution was added to each well in the same sequence as the addition of substrate solution. This causes the blue color to change to yellow. Plates were read within 50 minutes at 450 nm ($A_{450}$) using a plate reader. The absorbance of each plate was read as well.

Testing results of immune response to individual peptide by immunoenzymatic assay of individual antiserum presented as signal $A_{450}$ were analyzed and immune response was graded (Table 5).

The results of testing of the immune response of individual PEPTIDES SEQ ID NO: 6 to 21 are presented in Table 5.

TABLE 5

| PEPTIDE | OD 450 Mean values (n = 3-5) for dilution 1:10,000 | RANK |
| --- | --- | --- |
| SEQ ID NO: #6 | 0.096 | 17 |
| SEQ ID NO: #7 | 1.610 | 4 |
| SEQ ID NO: #8 | 0.097 | 16 |
| SEQ ID NO: #9 | 0.131 | 15 |
| SEQ ID NO: #10 | 9.212 | 3 |
| SEQ ID NO: #11 | 0.183 | 12 |
| SEQ ID NO: #12 | 0.661 | 9 |
| SEQ ID NO: #13 | 12.882 | 2 |
| SEQ ID NO: #14 | 0.394 | 11 |
| SEQ ID NO: #15 | 21.81 | 1 |
| SEQ ID NO: #16 | 0.823 | 6 |
| SEQ ID NO: #17 | 0.780 | 8 |
| SEQ ID NO: #18 | 0.138 | 13 |
| SEQ ID NO: #19 | 0.818 | 7 |
| SEQ ID NO: #20 | 0.138 | 14 |
| SEQ ID NO: #21 | 0.411 | 10 |
| SP35 reference peptide (positive control) | 18.135 | |

Conclusion: All 16 peptides tested fall in three groups. Group of relatively strong immunogenicity $A_{450}>1.0$ for dilution 1:1000 (SEQ ID NO: A7, 10, 13, 15). Group of intermediate immunogenicity $A_{450}>2.0$ for dilution 1:100 and $A_{450}<1.0$ for dilution 1:1000 (SEQ ID NO: 12, 14, 16, 17, 19, 21). Group of weak immunogenicity $A_{450}<2.0$ for dilution 1:100 remaining 5 peptides.

Method of Inducing Tumor and Treating with MMP-9 Oligopeptides

For testing the efficacy of selected peptides directed against MMP-9 in inducing tumors in mice, the following oligopeptides were selected from SEQ ID NO:6-21 (listed in Table 6): Mouse peptide SEQ ID NO:11 and SEQ ID NO:19 and Rat peptides SEQ ID NO: 7, SEQ ID NO:12 and SE ID NO:18.

The synthesized oligopeptides were biotinylated at N-terminal using four carbon spacers by Genscript (Pitcataway, N.J. 08554 USA) and conjugated to KLH protein. In an experiment performed on mice Male C57BL/6 were procured, immunized, tumor induced and observed for effectiveness of the treatment of oligopeptide-induced immunotherapy.

The injections were prepared using 100 μl 1 of KLH conjugated biotinylated peptides and 100 μl of complete Freund's adjuvant (Sigma, St. Louis, Mo.). Male C57BL/6 mice, 6 weeks of age on arrival were purchased from Simonsen Laboratories, Gilroy, Calif. and maintained in microisolator cage under pathogen-free conditions on a 12-h light/12-h dark schedule for a week. All animals were cared for in accordance with institutional guidelines for the care and use of experimental animals. After housing for a week, the mice (n=6/group) were immunized by intraperitoneal injection on Day 0, and incomplete Freund adjuvant (Sigma) on Day 7, 14 and 28. The blood samples were tested for their immune response by standard Elisa test using microtiter plates. Repeating injections of synthetic peptides in mice produce an immune response to specific individual peptides. Various dilutions were tried and examples of dilutions tried are 1:100, 1:1000 and 1:10000. The results of immune response to Mouse peptides #11 and #19 and Rat Peptides #7, 12 and 18 are presented in Table 6.

TABLE 6

ELISA assay of MMP-9 Mouse Peptides # SEQ ID NO:11 & # SEQ ID NO:19 and MMP-9 Rat Peptides
SEQ ID NO:7, # SEQ ID NO:12 and # SEQ ID NO:18 after immunization of C57BL/6 Male Mice

| Dilution | No Avidin 1 | No Peptide 2 | Control Sera 3 | MMP-9 Mouse Peptide SEQ ID NO:11 and 19 Sera m1, m2, m3 | | MMP-9 Rat Peptides # SEQ ID NO:7, 12 & 18 Sera m1-m6 | | | | |
|---|---|---|---|---|---|---|---|---|---|---|
| | | | | Peptide #11 | Peptide #19 | Peptide #7 | Peptide #12 | Peptide #18 | Peptide#18 | BL |
| 1-100 | C1 0.136 | 0.137 | 0.148 | m1 1.886 | m1 1.826 | m1 2.761 | m3 1.853 | m5 2.126 | m5 1.998 | BL 0.166 |
| 1-1000 | 0.127 | 0.129 | 0.133 | 1.8 | 2.287 | 2.861 | 1.803 | 1.615 | 1.749 | 0.13 |
| 1-10000 | 0.121 | 0.123 | 0.124 | 1.717 | 2.148 | 2.106 | 1.138 | 0.844 | 0.795 | 0.226 |
| 1-100 | c2 0.12 | 0.124 | 0.137 | m2 2.615 | m2 2.509 | m2 2.357 | m4 2.612 | m6 2.237 | BL 0.134 | BL 0.12 |
| 1-1000 | 0.115 | 0.115 | 0.12 | 2.63 | 2.52 | 2.355 | 2.415 | 2.031 | 0.117 | 0.117 |
| 1-10000 | 0.12 | 0.114 | 0.123 | 1.969 | 1.801 | 1.287 | 1.398 | 0.957 | 0.115 | 0.132 |
| 1-100 | | | | m3 2.349 | m3 2.405 | | | | | |
| 1-1000 | | | | 2.8 | 2.404 | | | | | |
| 1-10000 | | | | 2.197 | 1.813 | | | | | |
| 1-100 | | | | BL 0.491 | BL 0.122 | | | | | |
| 1-1000 | | | | 0.151 | 0.118 | | | | | |
| 1-10000 | | | | 0.122 | 0.134 | | | | | |

The level of immune response to all tested MMP-9 peptides was also evaluated in male B57BL/6 mice after they developed B16F0 melanoma tumors. The results of ELISA tests of sera obtained from tumor bearing mice are presented for mouse derived peptides #SEQ ID NO:11 and #SEQ ID NO:19 in Table 7 and for rat peptides #SEQ ID NO:7, #SEQ ID NO:12 and #SEQ ID NO:18 in Table 8.

TABLE 7

Immune response to MMP-9 Mouse Peptides 11 & 19 in B16FO Tumor Bearing
C57BL/6 Male Mice (ELISA assay)

| | No Avidin | No Peptide | Non Specific Peptide (cox2) | Control Sera | | | MMP-9 Mouse Peptide # SEQ ID NO:11 Sera m1-m6 | | | MMP-9 Mouse Peptide # SEQ ID NO:19 Sera m1-m6 | | |
|---|---|---|---|---|---|---|---|---|---|---|---|---|
| | 1 | 2 | 3 | 4 | 5 | 6 | 7 | 8 | 9 | 10 | 11 | 12 |
| 1-100 | 0.138 | 0.135 | 0.138 | 0.137 | 0.132 | 0.134 | m1 2.222 | m3 2.138 | m5 2.227 | m1 1.795 | m3 1.526 | m5 1.984 |
| 1-1000 | 0.128 | 0.126 | 0.129 | 0.131 | 0.138 | 0.123 | 2.603 | 2.559 | 2.649 | 1.983 | 1.916 | 1.664 |
| 1-10000 | 0.123 | 0.121 | 0.127 | 0.125 | 0.119 | 0.12 | 2.357 | 2.482 | 2.563 | 1.892 | 1.911 | 1.799 |
| 1-100 | 0.119 | 0.116 | 0.123 | 0.12 | 0.116 | 0.119 | m2 2.647 | m4 2.768 | m6 2.448 | m2 2.279 | m4 2.09 | m6 1.953 |
| 1-1000 | 0.12 | 0.115 | 0.126 | 0.117 | 0.114 | 0.116 | 1.223 | 2.611 | 2.126 | 2.45 | 2.155 | 2.167 |
| 1-10000 | 0.125 | 0.113 | 0.12 | 0.114 | 0.114 | 0.119 | 2.437 | 2.602 | 2.591 | 2.438 | 1.941 | 1.878 |

The results indicate that each of B16F0 tumor bearing mice had retained a strong immune response to mouse peptide #11 and #19 compared to control sera. There was no significant difference between immune response in mice immunized with peptide #11 and peptide #19.

TABLE 8

Immune response to MMP-9 Rat Peptides #7, #12, and #18 in B16FO Tumor Bearing C57BL/6 Male Mice (ELISA assay)

| | No Avidin | No Peptide | Control Sera | MMP-9 Rat Peptide# SEQ ID NO:7 Sera m1-m6 | | | MMP-9 Rat Peptide# SEQ ID NO:12 Sera m1-m6 | | | MMP-9 Rat Peptide # SEQ ID NO:18 Sera m1-m6 | | |
|---|---|---|---|---|---|---|---|---|---|---|---|---|
| 1-100 | 0.143 | 0.142 | 0.156 | m1 | m3 | m5 | m1 | m3 | m5 | m1 | m3 | m5 |
| | | | | 1.767 | 2.268 | 2.291 | 2.309 | 2.28 | 2.143 | 2.055 | 1.967 | 1.996 |
| 1-1000 | 0.142 | 0.131 | 0.143 | 2.467 | 2.929 | 2.713 | 2.553 | 2.582 | 2.981 | 2.411 | 2.403 | 2.02 |
| 1-10000 | 0.13 | 0.125 | 0.143 | 2.687 | 2.524 | 2.261 | 1.866 | 2.116 | 2.555 | 2.43 | 2.295 | 1.928 |
| 1-100 | 0.126 | 0.123 | 0.157 | m2 | m4 | m6 | m2 | m4 | m6 | m2 | m4 | m6 |
| | | | | 2.816 | 3.136 | 3.014 | 3.121 | 3.213 | 3.199 | 2.475 | 2.658 | 2.432 |
| 1-1000 | 0.128 | 0.12 | 0.138 | 3.056 | 2.964 | 3.083 | 3.273 | 3.126 | 2.908 | 2.807 | 2.795 | 2.504 |
| 1-10000 | 0.132 | 0.118 | 0.133 | 2.897 | 2.698 | 2.304 | 2.873 | 2.757 | 2.129 | 2.569 | 2.243 | 2.323 |

The results indicate that each of B16F0 tumor bearing mice had retained a strong immune response to tested rat peptides #SEQ ID NO:7, #SEQ ID NO:12 and #SEQ ID NO:18 compared to control sera and to sera of corresponding mice before melanoma cells inoculation (Table 6). The strongest response to peptide #SEQ ID NO:7 was observed in two mice (m4 and m6), to peptide #SEQ ID NO:12 in three mice (m3, m4 and m6) and to peptide #SEQ ID NO:18 in three mice (m2, m4 and m6). But overall there was no significant difference between immune response in all tested mice immunized with peptide #SEQ ID NO:7, #SEQ ID NO:12 and peptide #SEQ ID NO:18.

In another embodiment, substitution and omission may be carried out simultaneously. The oligopeptides may be further modified by repeating the sequences and combining more than one MMP-9 from mouse and rat for producing and formulating a vaccine. The peptidomimetic to the MMP's may be used to block the binding site of an over expressed MMP in a specific disease.

In one embodiment, the oligopeptide may be used as feedback regulators to specifically prevent or reduce the synthesis rate of MMP-9 productions at the cellular level. In one embodiment process of blocking and inhibition of ECM destruction by antigens produced due to vaccination of mice.

Figure 3:
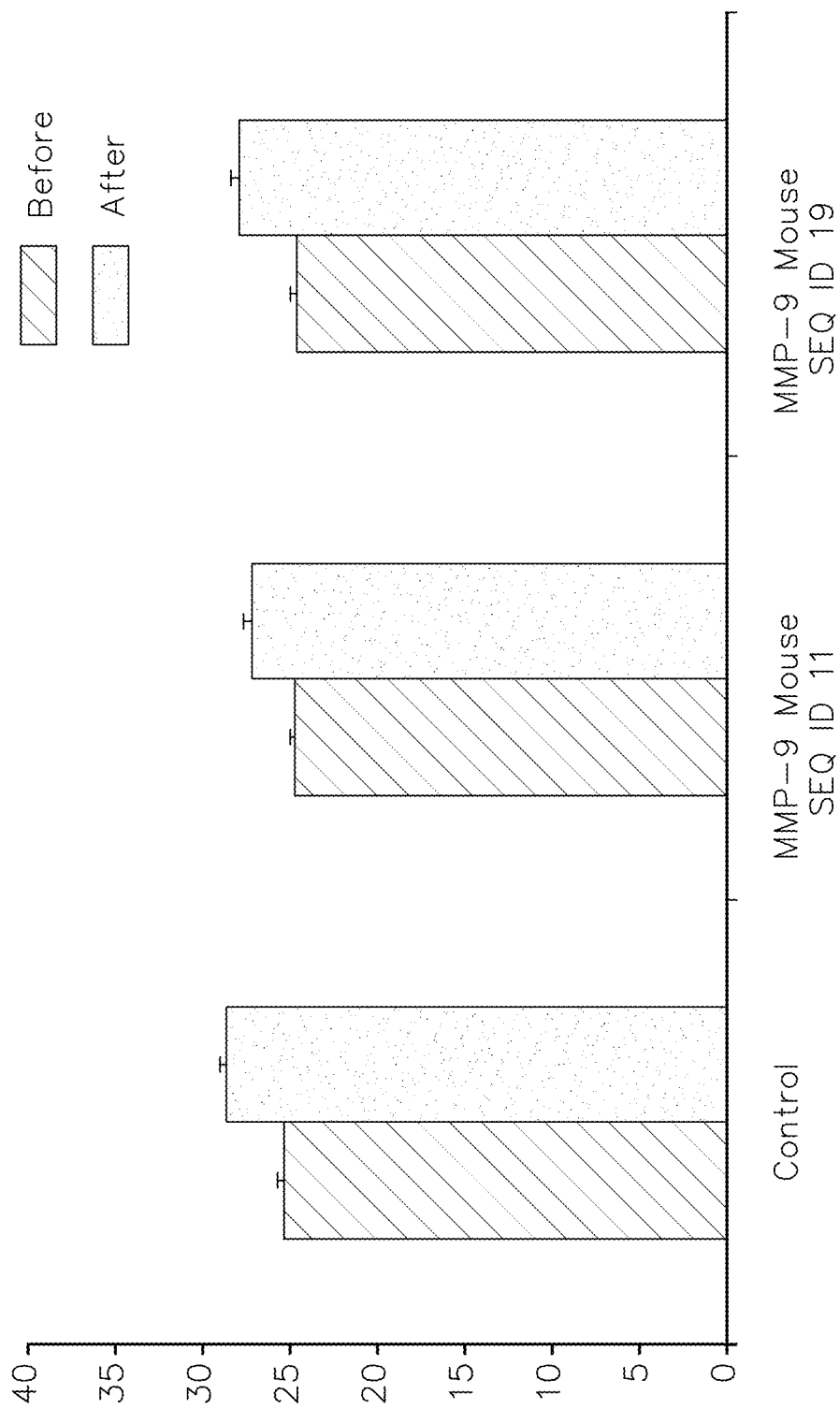
FIG. 3 shows Weight of Male C57BL/6 Mice Immunized with MMP-9 Mouse Peptides SEQ ID NO: A11 and A19 before and after B16F0 Melanoma Cells Xenograft.

FIG. 3 shows the weight of Male C57BL/6 Mice Immunized with MMP-9 Mouse Peptides SEQ ID NO: 11 and 19 before and after B16FO Melanoma Cells Xenograft. Control rats gained weight as the time progressed. MMP-9 Mouse SEQ ID NO:11 and 19 show similar results even after the tumor growth. There is negative effect of the vaccine and the rats seem to gain weight that is correlated to the age of the mice.

Figure 4:
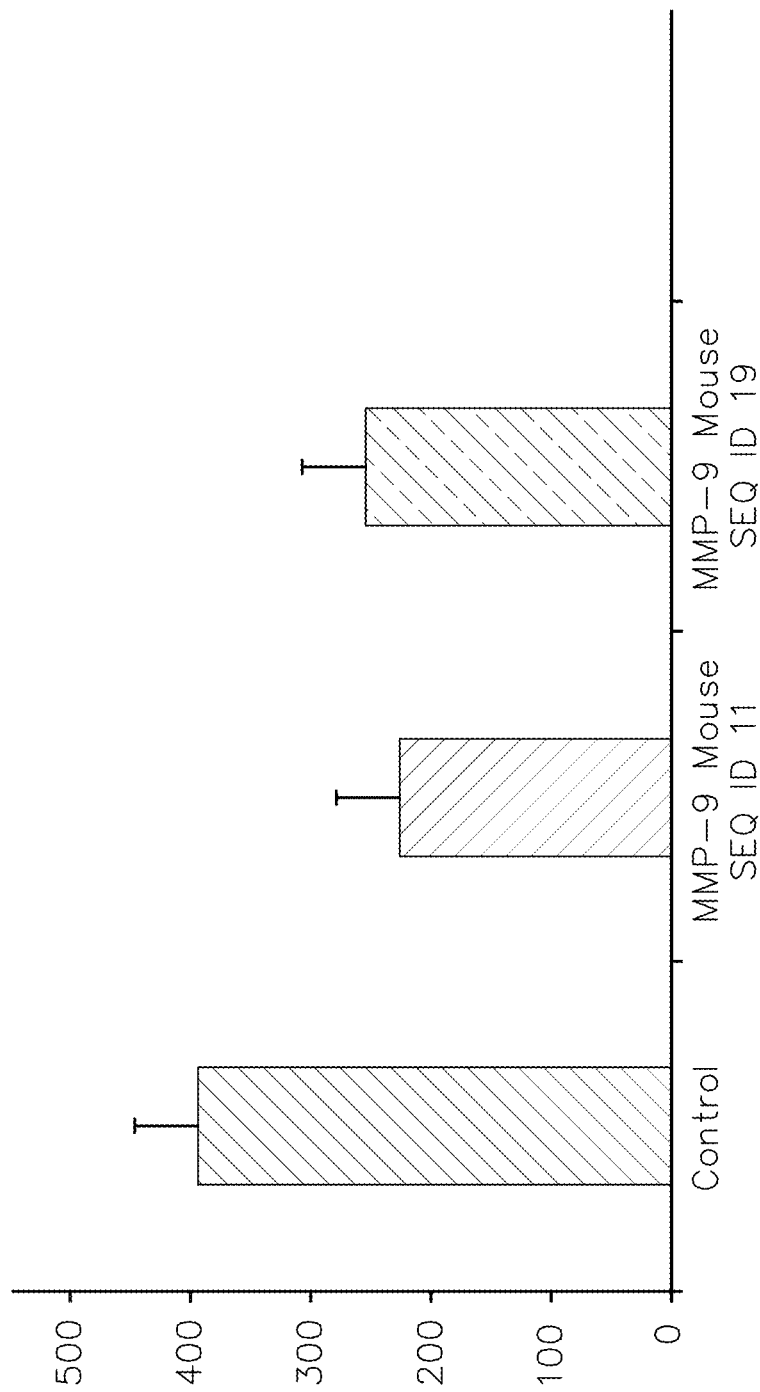
FIG. 4 shows Effect of Immunizing MMP-9 Mouse Peptides SEQ ID NO: A11 and A19 on Tumor Burden Inhibition of Melanoma Cells B16F0 Xenograft in Male C57BL/6 Mice.

FIG. 4 shows the effect of immunizing MMP-9 Mouse Peptides SEQ ID NO: 11 and 19 on tumor burden inhibition of Melanoma Cells B16F0 Xenograft in Male C57BL/6 Mice. There is approximately 40% and 30% reduction in tumor burden due to the treatment with MMP-9 mouse peptide SEQ ID NO:11 and SEQ ID NO:19. This is a significant reduction and results are very encouraging.

Figure 5:
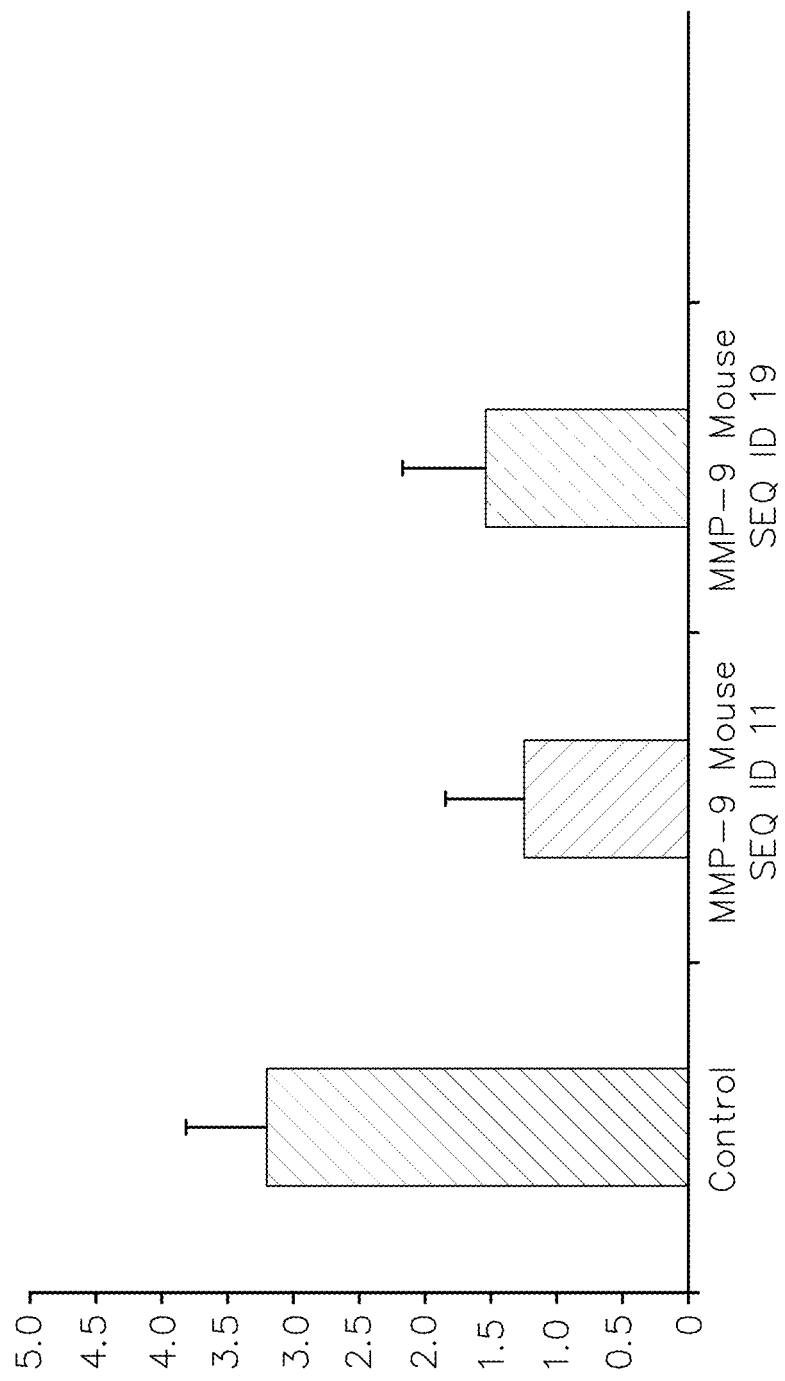
FIG. 5 shows Effect of Immunizing MMP-9 Mouse Peptides SEQ ID NO: A11 and A19 on Tumor Weight Inhibition of Melanoma Cells B16F0 Xenograft in Male C57BL/6 Mice.

FIG. 5 shows the effect of Immunizing MMP-9 Mouse Peptides SEQ ID NO: 11 and 19 on Tumor Weight Inhibition of Melanoma Cells B16F0 Xenograft in Male C57BL/6 Mice. The weight reduction of tumor is approximately 60% for SEQ ID NO: 11 and 50% for SEQ ID NO: 19. There is significant difference in tumor weight inhibition showing efficacies effect of the MMP-9 sequence treatment to reduce cancer tumor.

Figure 6:
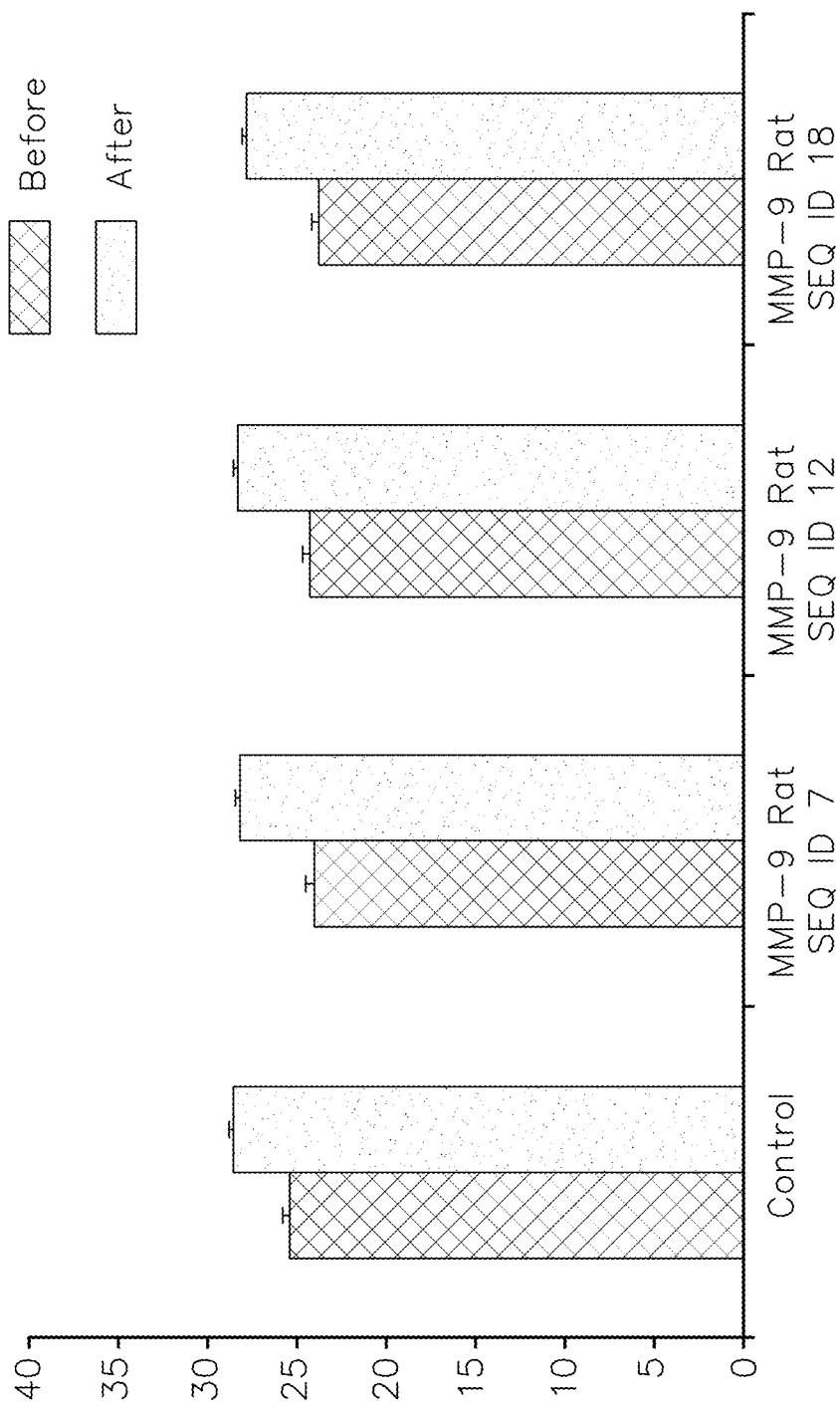
FIG. 6 shows Weight of Male C57BL/6 Mice Immunized with MMP-9 Rat Peptides SEQ ID NO: A7, A12 and A18 before and after B16F0 Melanoma Cells Xenograft.

FIG. 6 shows uniform weight gain of Male C57BL/6 Mice Immunized with MMP-9 Rat Peptides SEQ ID NO: 7, 12 and 18 before and after B16F0 Melanoma Cells Xenograft as compared to controls of the same period. Lack of loss of weight in tumor having rats and after their treatment is similar to control rats of the same age and time. This results is very encouraging to show that in spite of cancer the animals did not show a significant drop in weight to corroborate the beneficial effect of the vaccine. Albeit the weight gain may be due to the tumor as well which can be seen in before treatment rats having lower weight than the after the treatment rats having almost equal weight gain as the controls.

Figure 7:
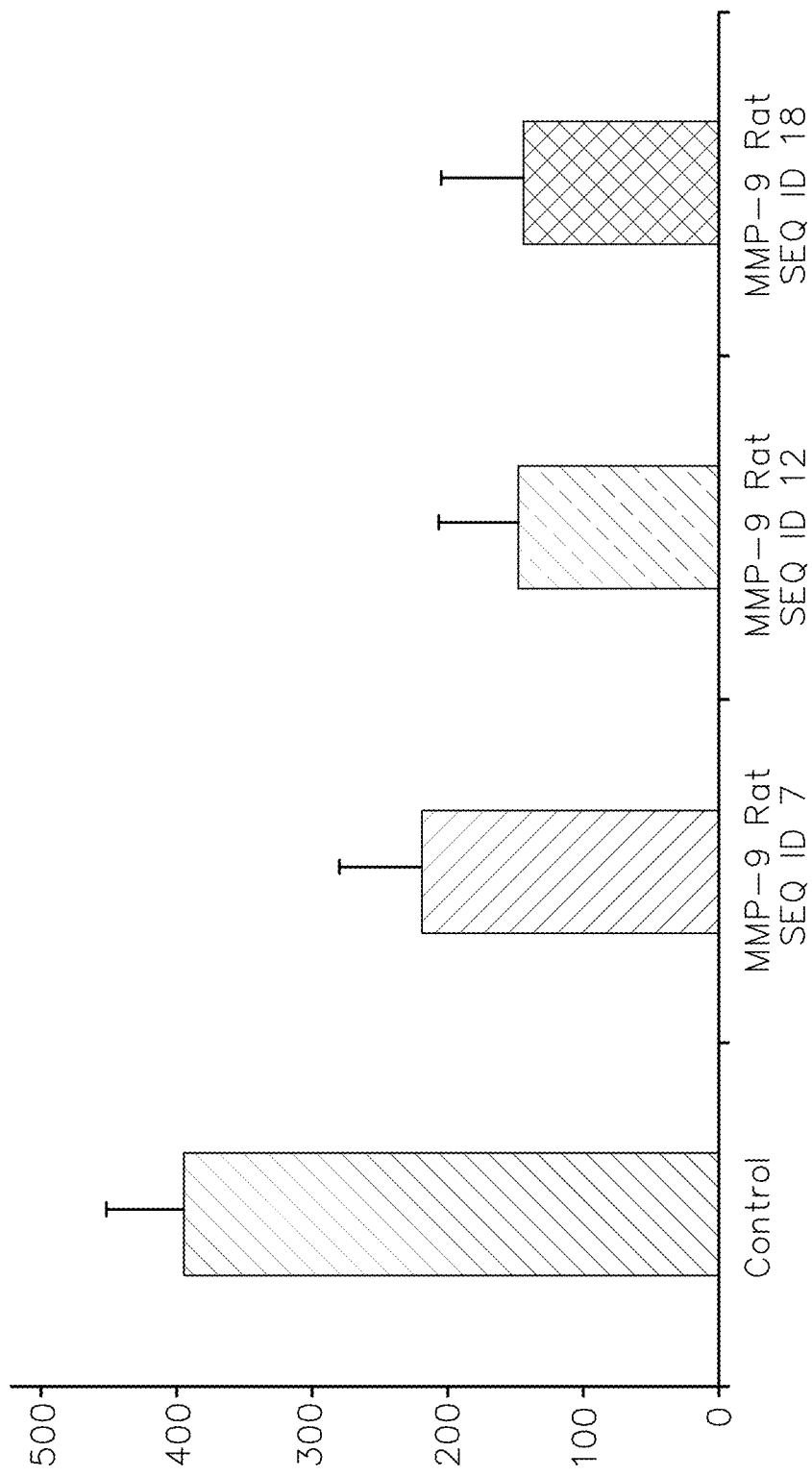
FIG. 7 shows Effect of Immunizing MMP-9 Rat Peptides SEQ ID NO: A7, A12 and A18 on Tumor Burden Inhibition of Melanoma Cell B16F0 Xenograft in Male B16F0 Mice.

FIG. 7 shows effect of immunizing MMP-9 rat peptides SEQ ID NO: #7, 12 and 18. SEQ ID 12 and 18 show more than 30% tumor burden inhibition compared to the control animals (mice). SEQ ID NO: 7 has 50% inhibition. The efficacy of SEQ ID NO: 12 and 18 are more than SEQ ID NO:7, but all three of them have inhibitory effect for tumor burden.

Figure 8:
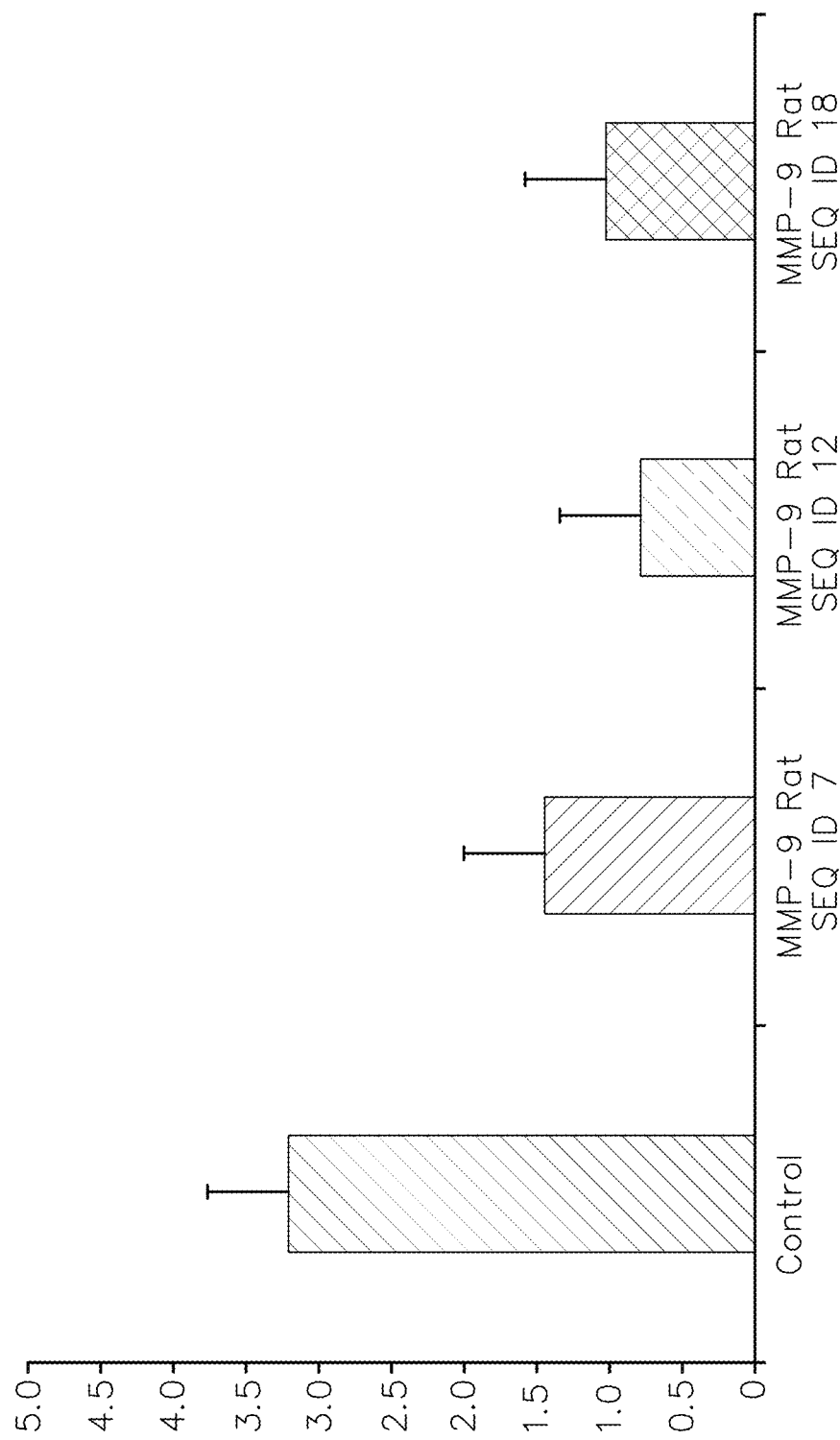
FIG. 8 shows Effect of Immunizing MMP-9 Peptides SEQ ID NO: A7, A12 and A18 on Tumor Weight Inhibition of Melanoma Cell B16F0 Xenograft in Male B16F0 Mice.
Figure 9:
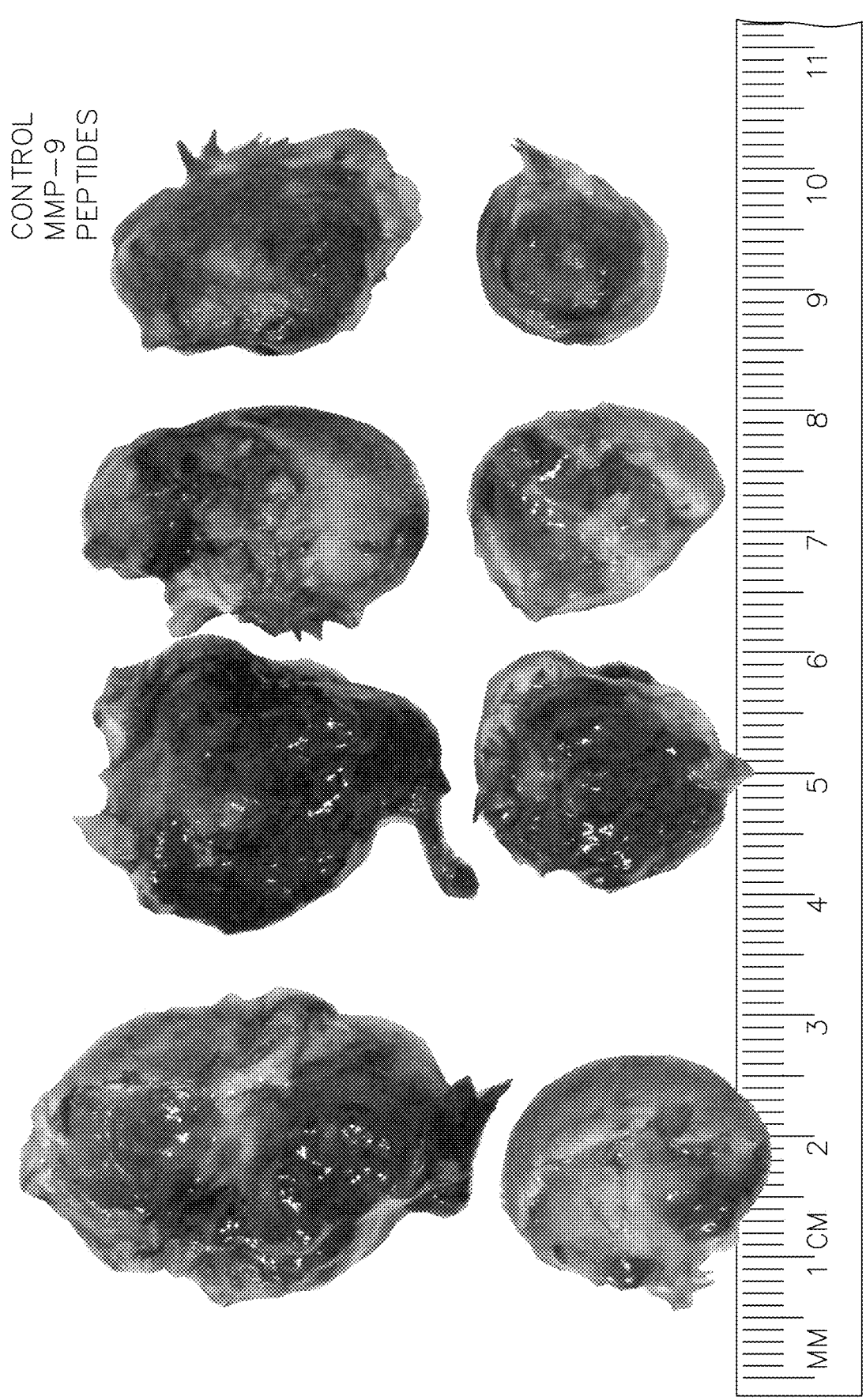
FIG. 9 shows the actual tumors that were induced in control animals after the treatment duration.
Figure 10:
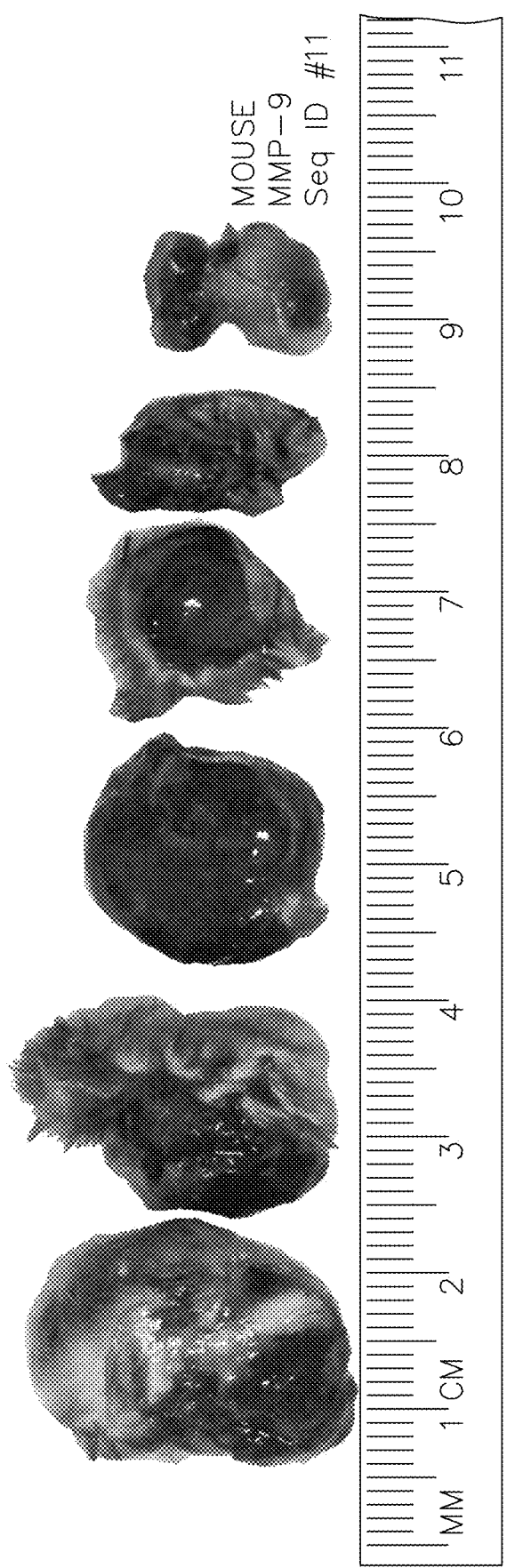
FIG. 10 shows tumor size reduction for MMP-9 treated mouse with SEQ ID NO: 11 peptides.
Figure 11:
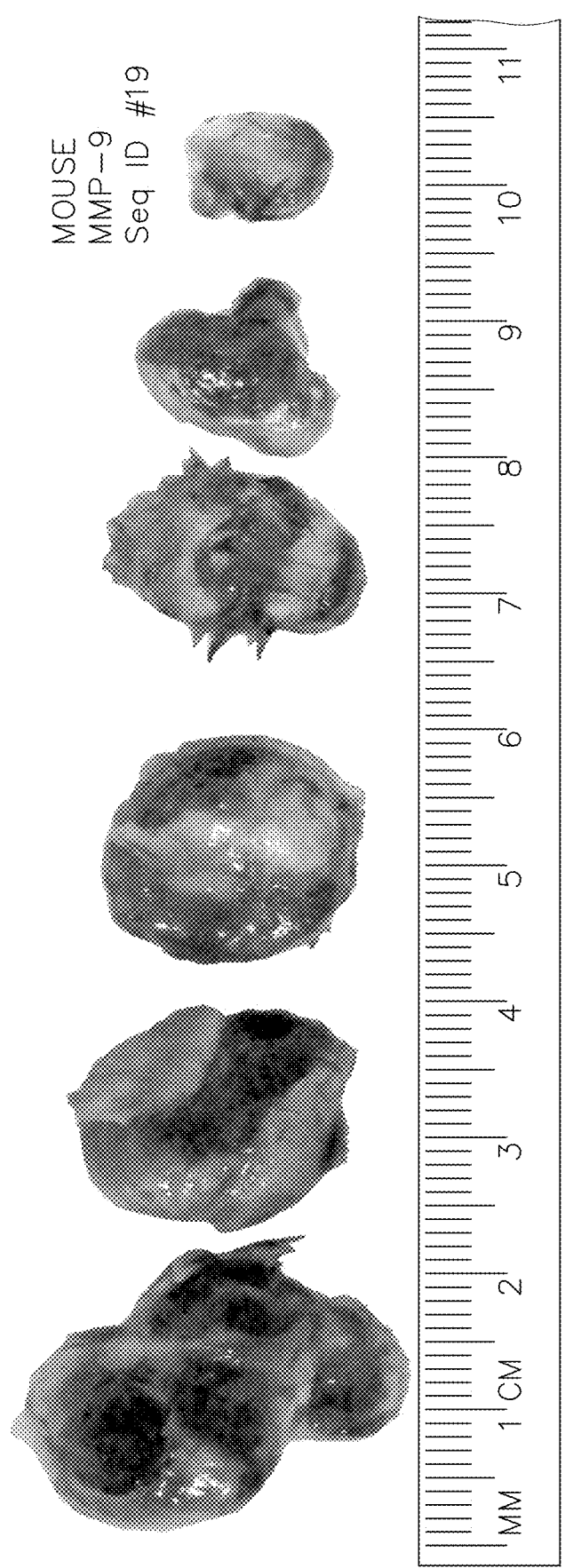
FIG. 11 shows tumor size reduction for MMP-9 treated mouse with SEQ ID NO: 19 peptides.
Figure 12:
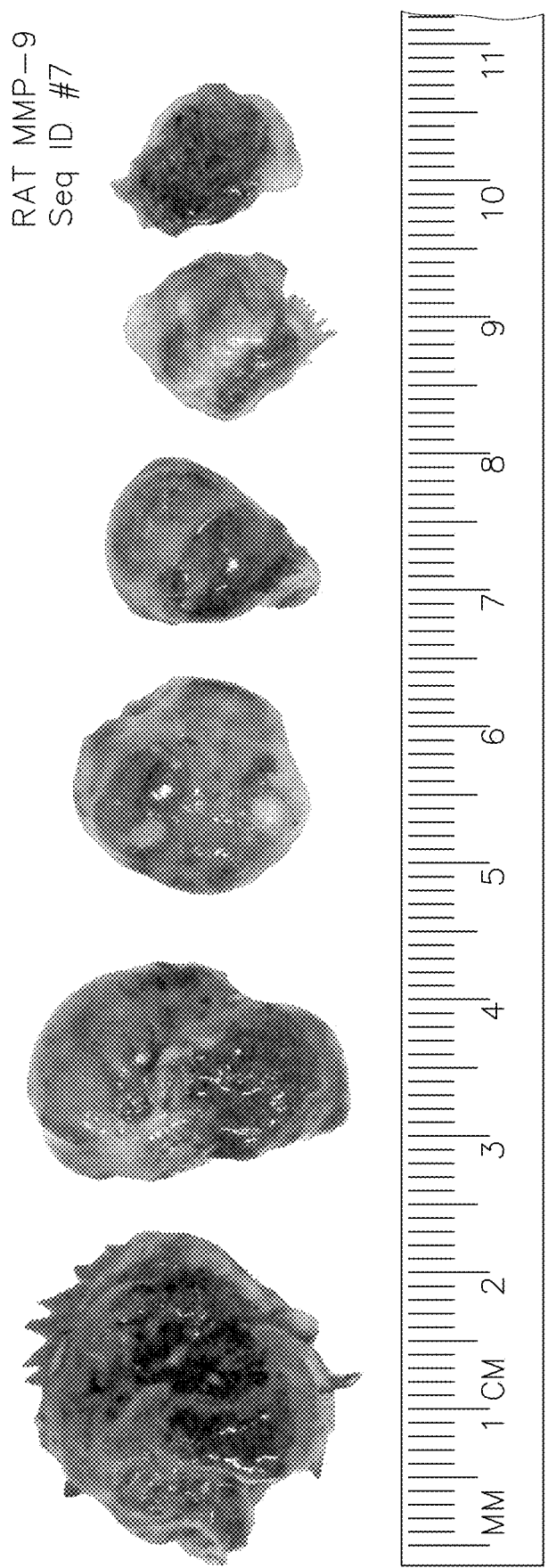
FIG. 12 shows tumor size reduction for MMP-9 treated rat with SEQ ID NO: 7 peptides.
Figure 13:
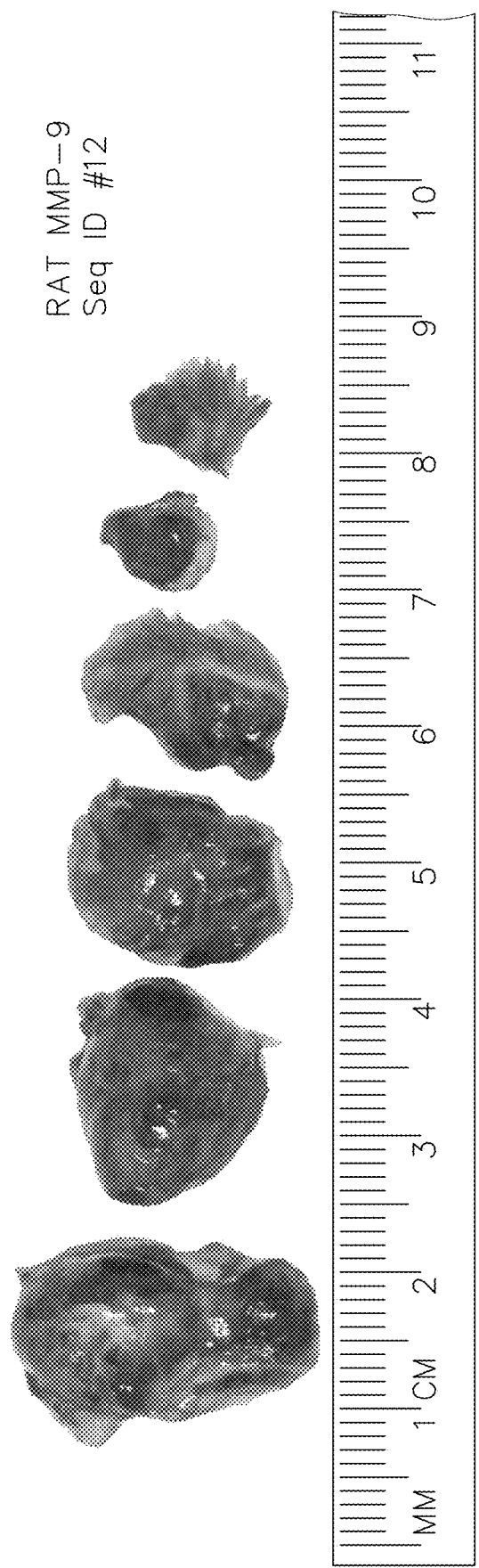
FIG. 13 shows tumor size reduction for MMP-9 treated rat with SEQ ID NO: 12 peptides.
Figure 14:
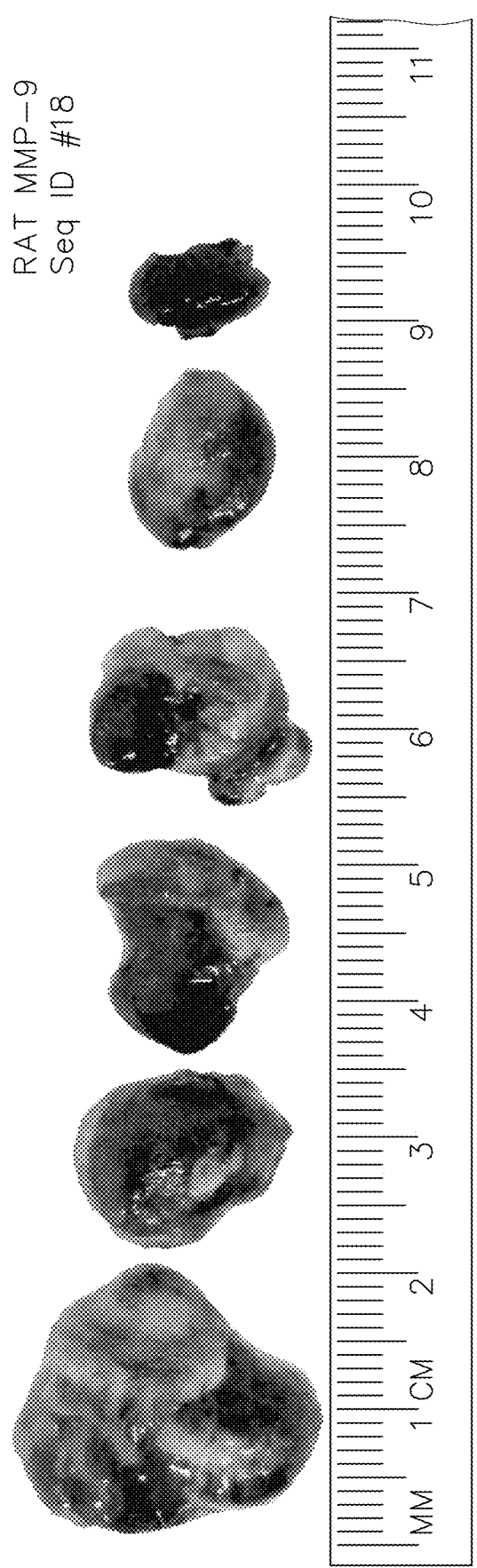
FIG. 14 shows tumor size reduction for MMP-9 treated rat with SEQ ID NO: 18 peptides.

FIG. 8 shows Effect of Immunizing MMP-9 Peptides SEQ ID NO: 7, 12 and 18 on Tumor Weight Inhibition of Melanoma Cell B16F0 Xenograft in Male B16F0 Mice. More than 70% reduction in tumor weight is seen by treating with SEQ ID NO:12 and 60% reduction in tumor size is observed using SEQ ID NO:18. SEQ ID NO: 7 has significant reduction at about 50%. As shown in FIG. 8 all the MMP-9 oligopeptides as vaccines are very effective in reducing the tumor weight, showing a promising treatment method, composition and use of MMP-9 oligopeptides for cancer treatment as vaccines in mammals.

FIGS. 9 to 14 show different tumor such as control mouse tumor and SEQ ID NO: 7, 12, 18, 11 and 19. There different effects of each peptide treatment in rat and mouse. The tumor size has decreased in all the treatment groups compared to controls.

The oligopeptide therapeutically effective amount may be administered to the mammal in many different ways and may not be limited to injections. The various methods of administration are well known in the art and some of the methods are described below.

A "specific species" to be treated by the subject method may mean a human or non-human animal, such as mouse, farm animals, primates and vertebrates.

The specific diseases that would be target diseases for a treatment using MMP oligopeptide sequences and/or peptidomimetic are neoplastic diseases, inflammatory diseases, coronary artery diseases, occlusive cardiovascular diseases, degenerative diseases and infectious diseases. Some examples of neoplastic diseases may be, but not limited to, cancer, lymphoma, leukemia, and brain tumor. Some examples of inflammatory diseases may be, but not limited to, arthritis, asthma, atherosclerosis, Crohn's disease, colitis, dermatitis, lupus erythematous etc. Some examples of infectious diseases may include, but not limited to, are bacterial, viral, fungal, mycoplasmal, certain genetic diseases and other infections. In the instant application, signal oligopeptides within the selective MMP protein that mediate MMP protein's key pathological function, namely the digestion of the connective tissue, which is a precondition for cancer cells to migrate and metastasize were identified. The oligopeptides were synthesized, the animals were injected and antibodies were raised. The tumor size was significantly reduced using these oligopeptide raised vaccines. The degree of efficacy can be seen by the titer level caused by MMP oligopeptide vaccine which proves the vaccines were very effective.

One of the conventional methods of choice to increase the natural antigenicity of the oligopeptide sequence(s) of a given protein is a slight alteration in the amino acid sequence within the given oligopeptide, i.e. by substitutions, deletions, insertions etc. of individual amino acids. The SEQ ID NO:6-21 were identified and designed in such a way that it matches the hydrophobicity, hydrophylicity and the electrical charge of the amino acids oligopeptide sequences of SEQ ID NO: A1-A3 (MMP) as shown in the previous application. It also maintains the signal characteristics and functionality as an epitope. The SEQ ID NO:7, 11, 12, 18 and 19 enhances the therapeutic efficacy for cross species immunization by enhancing natural antigenicity irrespective of whether the adjuvants are used.

Drug formulations suitable for these administration routes can be produced by adding one or more pharmacologically acceptable carriers to the agent and then treating the mixture through a routine process known to those skilled in the art. The mode of administration includes, but not limited to, are non-invasive peroral, topical (example transdermal), enteral, transmucosal, targeted delivery, sustained release delivery, delayed release, pulsed release and parenteral methods. Peroral administration may be administered both in liquid and dry state.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a subject composition as an active ingredient. Subject compositions may also be administered as a bolus, electuary, or paste.

When an oral solid drug product is prepared, oligopeptide sequence of MMP and/or a peptidomimetic of the MMP's is mixed with an excipient (and, if necessary, one or more additives such as a binder, a disintegrant, a lubricant, a coloring agent, a sweetening agent, and a flavoring agent), and the resultant mixture is processed through a routine method, to thereby produce an oral solid drug product such as tablets, coated tablets, granules, powder, or capsules. Additives may be those generally employed in the art. Examples of the excipient include lactate, sucrose, sodium chloride, glucose, starch, calcium carbonate, kaolin, microcrystalline cellulose, and silicic acid; examples of the binder include water, ethanol, propanol, simple syrup, glucose solution, starch solution, liquefied gelatin, carboxymethylcellulose, hydroxypropylcellulose, hydroxypropyl starch, methyl cellulose, ethyl cellulose, shellac, calcium phosphate, and polyvinyl pyrrolidone; examples of the disintegrant include dried starch, sodium arginate, powdered agar, sodium hydrogencarbonate, calcium carbonate, sodium lauryl sulfate, monoglyceryl stearate, and lactose; examples of the lubricant include purified talc, stearic acid salts, borax, and polyethylene glycol; and examples of the sweetening agent include sucrose, orange peel, citric acid, and tartaric acid.

When a liquid drug product for oral administration is prepared, oligopeptide sequence of MMP and/or a peptidomimetic of MMP's is mixed with an additive such as a sweetening agent, a buffer, a stabilizer, or a flavoring agent, and the resultant mixture is processed through a routine method, to thereby produce an orally administered liquid drug product such as an internal solution medicine, syrup, or elixir. Examples of the sweetening agent include vanillin; examples of the buffer include sodium citrate; and examples of the stabilizer include tragacanth, acacia, and gelatin.

For purposes of transdermal (e.g., topical) administration, dilute sterile, aqueous or partially aqueous solutions (usually in about 0.1% to 5% concentration), otherwise similar to the above parenteral solutions, may be prepared.

Formulations for rectal or vaginal administration may be presented as a suppository, which may be prepared by mixing a subject composition with one or more suitable non-irritating carriers comprising, for example, cocoa butter, polyethylene glycol, a suppository wax, or a salicylate, and which is solid at room temperature, but liquid at body temperature and, therefore, will melt in the appropriate body cavity and release the encapsulated compound(s) and composition(s). Formulations which are suitable for vaginal administration also include pessaries, tampons, creams, gels, pastes, foams, or spray formulations containing such carriers as are known in the art to be appropriate.

A targeted release portion can be added to the extended release system by means of either applying an immediate release layer on top of the extended release core; using coating or compression processes or in a multiple unit system such as a capsule containing extended and immediate release beads.

When used with respect to a pharmaceutical composition or other material, the term "sustained release" is art-recognized. For example, a therapeutic composition which releases a substance over time may exhibit sustained release characteristics, in contrast to a bolus type administration in which the entire amount of the substance is made biologically available at one time. For example, in particular embodiments, upon contact with body fluids including blood, spinal fluid, mucus secretions, lymph or the like, one or more of the pharmaceutically acceptable excipients may undergo gradual or delayed degradation (e.g., through hydrolysis) with concomitant release of any material incorporated therein, e.g., an therapeutic and/or biologically active salt and/or composition, for a sustained or extended period (as compared to the release from a bolus). This release may result in prolonged delivery of therapeutically effective amounts of any of the therapeutic agents disclosed herein.

Current efforts in the area of drug delivery include the development of targeted delivery in which the drug is only active in the target area of the body (for example, in cancerous tissues) and sustained release formulations in which the drug is released over a period of time in a controlled manner from a formulation. Types of sustained release formulations include liposomes, drug loaded biodegradable microspheres and drug polymer conjugates.

Delayed release dosage formulations are created by coating a solid dosage form with a film of a polymer which is insoluble in the acid environment of the stomach, but soluble in the neutral environment of the small intestines. The delayed release dosage units can be prepared, for example, by coating a drug or a drug-containing composition with a selected coating material. The drug-containing composition may be a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Alternatively, a delayed release tablet may be formulated by dispersing tire drug within a matrix of a suitable material such as a hydrophilic polymer or a fatty compound. Suitable hydrophilic polymers include, but are not limited to, polymers or copolymers of cellulose, cellulose ester, acrylic acid, methacrylic acid, methyl acrylate, ethyl acrylate, and vinyl or enzymatically degradable polymers or copolymers as described above. These hydrophilic polymers are particularly useful for providing a delayed release matrix. Fatty compounds for use as a matrix material include, but are not limited to, waxes (e.g. carnauba wax) and glycerol tristearate. Once the active ingredient is mixed with the matrix material, the mixture can be compressed into tablets.

A pulsed release-dosage is one that mimics a multiple dosing profile without repeated dosing and typically allows at least a twofold reduction in dosing frequency as compared to the drug presented as a conventional dosage form (e.g., as a solution or prompt drug-releasing, conventional solid dosage form). A pulsed release profile is characterized by a time period of no release (lag time) or reduced release followed by rapid drug release.

The phrases "parenteral administration" and "administered parenterally" as used herein refer to modes of administration other than enteral and topical administration, such as injections, and include without limitation intravenous, intramuscular, intrapleural, intravascular, intrapericardial, intra-arterial, intrathecal, intracapsular, intraorbital, intracardiac, intradennal, intraperitoneal, transtracheal, subcutaneous, subcuticular, intra-articular, subcapsular, subarachnoid, intraspinal and intrastemal injection and infusion.

Certain pharmaceutical compositions disclosed herein suitable for parenteral administration comprise one or more subject compositions in combination with one or more pharmaceutically acceptable sterile, isotonic, aqueous, or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic within the blood of the intended recipient or suspending or thickening agents.

When an injection product is prepared, oligopeptide sequence of MMP and/or a peptidomimetic of MMP's is mixed with an additive such as a pH regulator, a buffer, a stabilizer, an isotonicity agent, or a local anesthetic, and the resultant mixture is processed through a routine method, to thereby produce an injection for subcutaneous injection, intramuscular injection, or intravenous injection. Examples of the pH regulator or buffer include sodium citrate, sodium acetate, and sodium phosphate; examples of the stabilizer include sodium pyrosulfite, EDTA, thioglycollic acid, and thiolactic acid; examples of the local anesthetic include procaine hydrochloride and lidocaine hydrochloride; and examples of the isotonicity agent include sodium chloride and glucose.

Adjuvants are used to enhance the immune response. Various types of adjuvants are available. Haptens are used as adjuvants in this disclosure. Freund's adjuvants may also be used to produce water-in-oil emulsions of immunogens. Antigens in water-in-oil emulsions stimulate high and long-lasting antibody responses which can be attributed to the slow release of antigen. Antigens (preferably in saline) are typically mixed with an equal volume of the adjuvant to form an emulsion.

The phrase "pharmaceutically acceptable" is art-recognized. In certain embodiments, the term includes compositions, polymers and other materials and/or dosage forms which are within the scope of sound medical judgment, suitable for use in contact with the tissues of mammals, human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, solvent or encapsulating material involved in carrying or transporting any subject composition, from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

In certain embodiments, the pharmaceutical compositions described herein are formulated in a manner such that said compositions will be delivered to a mammal in a therapeutically effective amount, as part of a prophylactic, preventive or therapeutic treatment.

In certain embodiments, the dosage of the oligopeptide compositions, which may be referred as therapeutic composition provided herein may be determined by reference to the plasma concentrations of the therapeutic composition or other encapsulated materials. For example, the blood samples may be tested for their immune response to their corresponding oligopeptides.

The therapeutic compositions provided by this application may be administered to a subject in need of treatment by a variety of conventional routes of administration, including orally, topically, parenterally, e.g., intravenously, subcutaneously or intramedullary. Further, the therapeutic compositions may be administered intranasally, as a rectal suppository, or using a "flash" formulation, i.e., allowing the medication to dissolve in the mouth without the need to use water. Furthermore, the compositions may be administered to a subject in need of treatment by controlled release dosage forms, site specific drug delivery, transdermal drug delivery, patch (active/passive) mediated drug delivery, by stereotactic injection, or in nanoparticles.

Expressed in terms of concentration, an active ingredient can be present in the therapeutic compositions of the present invention for localized use about the cutis, intranasally, pharyngolaryngeally, bronchially, intravaginally, rectally, or ocularly.

For use as aerosols, the active ingredients can be packaged in a pressurized aerosol container together with a gaseous or liquefied propellant, for example, dichlorodifluoromethane, carbon dioxide, nitrogen, propane, and the like, with the usual adjuvants such as cosolvents and wetting agents, as may be necessary or desirable.

The most common routes of administration also include the preferred transmucosal (nasal, buccal/sublingual, vaginal, ocular and rectal) and inhalation routes.

In addition, in certain embodiments, subject compositions of the present application maybe lyophilized or subjected to another appropriate drying technique such as spray drying. The subject compositions may be administered once, or may be divided into a number of smaller doses to be administered at varying intervals of time, depending in part on the release rate of the compositions and the desired dosage.

Formulations useful in the methods provided herein include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of a subject composition which may be combined with a carrier material to produce a single dose may vary depending upon the subject being treated, and the particular mode of administration.

The therapeutically acceptable amount described herein may be administered in inhalant or aerosol formulations. The inhalant or aerosol formulations may comprise one or more agents, such as adjuvants, diagnostic agents, imaging agents, or therapeutic agents useful in inhalation therapy. The final aerosol formulation may for example contain 0.005-90% w/w, for instance 0.005-50%, 0.005-5% w/w, or 0.01-1.0% w/w, of medicament relative to the total weight of the formulation.

Examples of suitable aqueous and non-aqueous carriers which may be employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity may be maintained, for example, by the use of coating materials, such as lecithin, by the maintenance of the required particle size in the case of dispersions, and by the use of surfactants. The therapeutic acceptable dosage may be combined with other drugs and may be treated as a combination drug.

In addition, it will be appreciated that the various sequences, immunization processes, and methods of treatment disclosed herein may be embodied using means for achieving the various combinations of therapeutic dosage and delivery methods to treat a specific disease such as cancer. Accordingly, the specification and drawings are to be regarded in an illustrative rather than a restrictive sense.

What is claimed is:

1. A method of inducing an immune response against human matrix metalloproteinase-9 (MMP-9) in a mammalian subject, said method comprising administering to said mammalian subject an effective amount of a composition comprising one or more of the peptides selected from the group consisting of the peptides set forth in the amino acid sequence of SEQ ID NOs: 7, 11, 12, 18, and 19 to elicit the production of antibodies against MMP-9.

2. The method of claim 1, wherein said antibodies are effective to block the enzymatic activity of MMP-9 and inhibit tumor cell invasion.

3. A method for suppressing the growth of an invasive tumor in a mammalian subject, said method comprising administering to said mammalian subject an effective amount of a composition comprising one or more peptides selected from the group consisting of the peptides set forth in the amino acid sequence of SEQ ID NOs: 7, 11, 12, 18, and 19 to elicit antibodies against human matrix metalloproteinase-9 (MMP-9) in the subject, wherein said antibodies are effective to block the enzymatic activity of MMP-9 and inhibit tumor cell invasion, thereby suppressing the growth of the tumor in said mammalian subject.

* * * * *

SEQUENCE LISTING

```
<160> NUMBER OF SEQ ID NOS: 17

<210> SEQ ID NO 1
<211> LENGTH: 8
<212> TYPE: PRT
<213> ORGANISM: Artificial Sequence
<220> FEATURE:
<223> OTHER INFORMATION: Mouse Synthetic OligoPeptide

<400> SEQUENCE: 1

Asp Lys Asp Gly Lys Phe Gly Phe
1               5

<210> SEQ ID NO 2
<211> LENGTH: 8
<212> TYPE: PRT
<213> ORGANISM: Artificial Sequence
<220> FEATURE:
<223> OTHER INFORMATION: Bovine Synthetic OligoPeptide

<400> SEQUENCE: 2

Asp Ala Asp Arg Gln Phe Gly Phe
1               5

<210> SEQ ID NO 3
<211> LENGTH: 8
```

```
<212> TYPE: PRT
<213> ORGANISM: Artificial Sequence
<220> FEATURE:
<223> OTHER INFORMATION: Rat Synthetic OligoPeptide

<400> SEQUENCE: 3

Asp Thr Asp Arg Lys Tyr Gly Phe
1               5

<210> SEQ ID NO 4
<211> LENGTH: 8
<212> TYPE: PRT
<213> ORGANISM: Artificial Sequence
<220> FEATURE:
<223> OTHER INFORMATION: CARP Synthetic OilgoPeptide

<400> SEQUENCE: 4

Asp Lys Asp Lys Ile Phe Gly Phe
1               5

<210> SEQ ID NO 5
<211> LENGTH: 8
<212> TYPE: PRT
<213> ORGANISM: Artificial Sequence
<220> FEATURE:
<223> OTHER INFORMATION: Pufferfish Synthetic OligoPeptide

<400> SEQUENCE: 5

Asp Lys Asp Lys Lys Tyr Gly Phe
1               5

<210> SEQ ID NO 6
<211> LENGTH: 8
<212> TYPE: PRT
<213> ORGANISM: Artificial Sequence
<220> FEATURE:
<223> OTHER INFORMATION: Rabbit Synthetic OligoPeptide

<400> SEQUENCE: 6

Asp Thr Asp Arg Arg Phe Gly Phe
1               5

<210> SEQ ID NO 7
<211> LENGTH: 8
<212> TYPE: PRT
<213> ORGANISM: Artificial Sequence
<220> FEATURE:
<223> OTHER INFORMATION: Mouse Synthetic OligoPeptide

<400> SEQUENCE: 7

Asp Lys Asp Gly Lys Phe Gly Phe
1               5

<210> SEQ ID NO 8
<211> LENGTH: 15
<212> TYPE: PRT
<213> ORGANISM: Artificial Sequence
<220> FEATURE:
<223> OTHER INFORMATION: Rat Synthetic OligoPeptide

<400> SEQUENCE: 8

Cys His Phe Pro Phe Thr Phe Glu Gly Arg Ser Tyr Leu Ser Cys
1               5                   10                  15

<210> SEQ ID NO 9
<211> LENGTH: 15
<212> TYPE: PRT
```

```
<213> ORGANISM: Artificial Sequence
<220> FEATURE:
<223> OTHER INFORMATION: Chicken Synthetic OligoPeptide

<400> SEQUENCE: 9

Cys His Phe Pro Phe Ile Phe Glu Gly Arg Ser Tyr Ser Arg Cys
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: EUROPEAN CARP Synthetic OligoPeptide

<400> SEQUENCE: 10

Cys His Phe Pro Phe Leu Phe Glu Gly Thr Ser Tyr Ser Ser Cys
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: PUFFERFISH Synthetic OligoPeptide

<400> SEQUENCE: 11

Cys His Phe Pro Phe Arg Phe Gln Asn Lys Pro Tyr Lys His Cys
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: FLOUNDER Synthetic OligoPeptide

<400> SEQUENCE: 12

Cys His Phe Pro Phe Thr Phe Glu Gly Lys Ser Tyr Thr Ser Cys
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: BOVINE Synthetic OligoPeptide

<400> SEQUENCE: 13

Asp Gln Asp Lys Leu Tyr Gly Phe Cys Pro Thr Arg Val Asp Ala
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: RAT Synthetic OligoPeptide

<400> SEQUENCE: 14

Asp Lys Ala Asp Gly Phe Cys Pro Thr Arg Ala Asp Val Thr Val
1               5                   10                  15

<210> SEQ ID NO 15
<211> LENGTH: 15
<212> TYPE: PRT
<213> ORGANISM: Artificial Sequence
```

```
-continued

<220> FEATURE:
<223> OTHER INFORMATION: RAT Synthetic OligoPeptide

<400> SEQUENCE: 15

Asp Gln Asp Lys Leu Tyr Gly Phe Cys Pro Thr Arg Val Asp Ala
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: CARP Synthetic OligoPeptide

<400> SEQUENCE: 16

Asp Lys Lys Tyr Gly Phe Cys Pro Asn Arg Asp Thr Ala Val Ile
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: RABBIT Synthetic OligoPeptide

<400> SEQUENCE: 17

Asp Lys Asp Lys Leu Tyr Gly Phe Cys Pro Thr Arg Ala Asp Ser
1               5                   10                  15
```